United States Patent [19]

Fischer et al.

[11] Patent Number: 5,672,718

[45] Date of Patent: Sep. 30, 1997

[54] N-PHENYLACETAMINO NITRILES

[75] Inventors: Reiner Fischer, Monheim; Gunther Beck, Leverkusen, both of Germany

[73] Assignee: Bayer Aktiengesellschaft, Leverkusen, Germany

[21] Appl. No.: 558,300

[22] Filed: Nov. 15, 1995

Related U.S. Application Data

[62] Division of Ser. No. 140,633, Oct. 21, 1993, Pat. No. 5,508,436.

[30] Foreign Application Priority Data

Oct. 28, 1992 [DE] Germany ............ 42 36 400.0

[51] Int. Cl.$^6$ .................................. C07D 333/20
[52] U.S. Cl. ................. 549/28; 549/61; 549/69; 549/363; 549/424; 549/449
[58] Field of Search ............... 549/28, 61, 69, 549/363, 424, 449

[56] References Cited

FOREIGN PATENT DOCUMENTS

| | | |
|---|---|---|
| 427907 | 5/1991 | European Pat. Off. . |
| 456063 | 11/1991 | European Pat. Off. . |
| 419457 | 11/1934 | United Kingdom . |

OTHER PUBLICATIONS

Chemical Abstracts 28–Heterocyclic Compounds, p.1243, vol. 68, (1968); 12942a; "Lactams. X. The Synthesis of . . . ", VG Granik et al. dl–a–Aminophenylacetic Acid, RE Steiger, pp. 23–25.
Liebighs Ann. Chem., vol. 764, pp. 69–93, (1972); "Enamide", P. Kurtz, et al.
J. Org. Chem, vol. 43, No. 13, (1978), pp. 2576–2581; "Approach to the Use of Benzylpenicilliancylase for . . . " D. Rossi, et al.

Primary Examiner—Jacqueline Haley
Attorney, Agent, or Firm—Sprung Horn Kramer & Woods

[57] ABSTRACT

The present invention relates to novel N-phenylacetamino nitriles of the general formula (I),

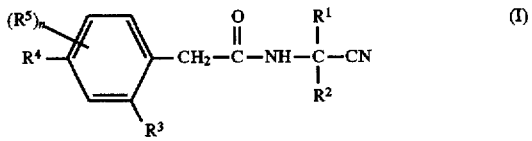

in which $R^1$ represents hydrogen, or represents alkyl, alkenyl, cycloalkyl, aryl or heterocyclyl which are in each case optionally substituted, and $R^2$ represents hydrogen, or represents alkyl which is optionally substituted, or $R^1$ and $R^2$, together with the carbon atom to which they are bonded, represent cycloalkyl or heterocyclyl which are in each case optionally substituted, $R^3$ represents halogen, alkyl or alkoxy, $R^4$ represents hydrogen, halogen, alkyl, halogenoalkyl or alkoxy, $R^5$ represents halogen, alkyl or alkoxy, and m represents a number 0, 1, 2 or 3, processes for their preparation and their use for the preparation of agents for controlling pests.

12 Claims, No Drawings

N-PHENYLACETAMINO NITRILES

This application is a divisional of application Ser. No. 08/140,633, filed Oct. 21, 1993 now U.S. Pat. No. 5,508,436.

The invention relates to novel N-phenylacetamino nitriles, a process for their preparation and their use as intermediates for the synthesis of insecticidal, acaricidal and herbicidal 3-aryl-pyrrolidine-2,4-diones.

The preparation of 3-aryl-pyrrolidine-2,4-diones from N-phenylacetamino carboxylic acid esters is known (cf., e.g. EP 456 063). The N-phenylacetamino carboxylic acid esters which are required as precursors for this preparation are obtained, as a rule, with the aid of a 4-stage reaction sequence, in which the corresponding amino acids are initially prepared, and isolated, in two stages via ketone and amino nitrile intermediates, and then either initially acylated and then esterified or first esterified and subsequently acylated (cf., e.g., Indian J. Chem. 6, 341–345 ([1968]; EP 456 063).

The preparation of N-phenylacetamino nitriles by reacting amino nitriles with phenylacetyl chlorides in the presence of bases is likewise known (cf., e.g., J. Org. Chem. 43, 2576–2581 ([1978]).

Novel N-phenylacetamino nitriles of the general formula (I) have been found

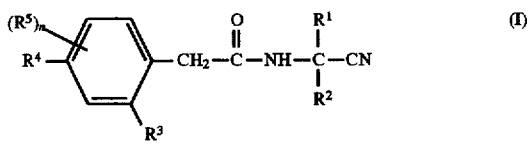

in which
R¹ represents hydrogen, or represents alkyl, alkenyl, cycloalkyl, aryl or heterocyclyl which are in each case optionally substituted, and
R² represents hydrogen, or represents alkyl which is optionally substituted, or
R¹ and R² together with the carbon atom to which they are bonded, represent cycloalkyl or heterocyclyl which are in each case optionally substituted,
R³ represents halogen, alkyl or alkoxy,
R⁴ represents hydrogen, halogen, alkyl, halogenoalkyl or alkoxy,
R⁵ represents halogen, alkyl or alkoxy, and
n represents a number 0, 1, 2 or 3.

The compounds of the formula (I) can optionally, depending on the nature of the substituents, be present as optical isomers or isomeric mixtures of varying composition. Both the pure isomers and the isomeric mixtures are claimed according to the invention.

It has furthermore been found that the novel N-phenylacetamino nitriles of the general formula (I)

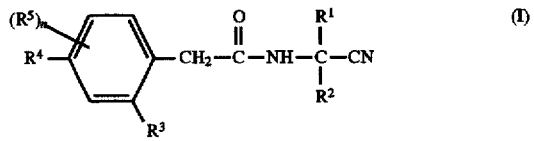

in which
R¹ represents hydrogen, or represents alkyl, alkenyl, cycloalkyl, aryl or heterocyclyl which are in each case optionally substituted, and
R² represents hydrogen, or represents alkyl which is optionally substituted, or
R¹ and R² together with the carbon atom to which they are bonded, represent cycloalkyl or heterocyclyl which are in each case optionally substituted,
R³ represents halogen, alkyl or alkoxy,
R⁴ represents hydrogen, halogen, alkyl, halogenoalkyl or alkoxy,
R⁵ represents halogen, alkyl or alkoxy, and
n represents a number 0, 1, 2 or 3,
are obtained if α-amino nitriles of the formula (II),

in which
R¹ and R² have the abovementioned meaning,
are reacted with phenylacetyl halides of the formula (III),

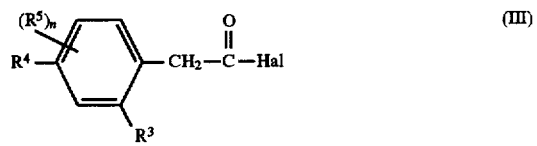

in which
R³, R⁴, R⁵ and n have the abovementioned meaning, and
Hal represents halogen,
optionally in the presence of a diluent and optionally in the presence of a reaction aid.

It has been found, finally, that the novel N-phenylacetamino nitriles of the formula (I) are outstandingly suitable as readily available intermediates for the synthesis of insecticidal, acaricidal and herbicidal 3-aryl-pyrrolidine-2,4-diones, whereby they are initially reacted in a first stage with alcohols of the formula (IV),

in which
R represents alkyl,
optionally in the presence of a diluent and optionally in the presence of sulphuric acid as a reaction aid, and the N-phenylacetamino carboxylic acid esters of the formula (V) thereby obtained,

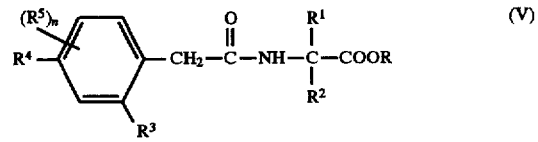

in which
R, R¹, R², R³, R⁴, R⁵ and n have the abovementioned meaning,
are cyclised in a subsequent second stage, optionally in the presence of a diluent and optionally in the presence of a reaction aid.

In this context, it was particularly surprising that the reaction of the N-phenylacetamino nitriles of the formula (I) with alcohols of the formula (IV), in the presence of sulphuric acid as a reaction aid, yielded the desired N-phenylacetamino carboxylic acid esters of the formula (V) in high yield and purity, since a corresponding reaction using hydrochloric acid as the reaction aid, in analogy with processes known from the literature (cf., e.g., Khim. Farm. Zh. 1, 21–26 [1967] and CA 68: 12942a), did not yield the desired products.

It turns out to be a particular advantage of this approach that, in the synthesis of the 3-aryl-pyrrolidine-2,4-diones which are desired as end products, the amino acid intermediate, which gives rise to particular problems during the isolation and purification on account of its zwitterionic character, no longer arises and that, in addition, the total synthesis is reduced from four to three stages.

The N-phenylacetamino nitriles according to the invention are generally defined by the formula (I). Compounds of the formula (I) are preferred in which $R^1$ represents hydrogen, in each case straight-chain or branched alkyl having 1 to 12 carbon atoms, alkenyl having 3 to 8 carbon atoms, halogenoalkyl having 1 to 8 carbon atoms and 1 and 17 identical or different halogen atoms, alkoxyalkyl having in each case 1 to 8 carbon atoms in the individual alkyl moieties, alkoxyalkoxyalkyl having in each case 1 to 8 carbon atoms in the individual alkyl moieties, alkylthioalkyl having in each case 1 to 8 carbon atoms in the individual alkyl moieties, cycloalkyl having 3 to 8 carbon atoms, saturated heterocyclyl having 3 to 8 ring members and 1 to 2 identical or different heteroatoms—in particular nitrogen, oxygen and/or sulphur—or represents arylalkyl or aryl, in each case having 6 to 10 carbon atoms in the aryl moiety and, where appropriate, 1 to 6 carbon atoms in the straight-chain or branched alkyl moiety, or heteroaryl, having 2 to 9 carbon atoms and 1 to 4 identical or different heteroatoms—in particular nitrogen, oxygen and/or sulphur, which are in each case optionally substituted identically or differently once or more than once in the aryl or heteroaryl moiety, where suitable aryl or heteroaryl substituents in each case are:

Halogen, nitro, in each case straight-chain or branched alkyl, alkoxy, alkylthio, alkylsulphinyl or alkylsulphonyl having in each case 1 to 6 carbon atoms, as well as in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, and $R^2$ represents hydrogen, in each case straight-chain or branched alkyl having 1 to 12 carbon atoms, halogenoalkyl having 1 to 8 carbon atoms and 1 to 17 identical or different halogen atoms, or alkoxyalkyl having in each case 1 to 8 carbon atoms in the individual alkyl moieties, or $R^1$ and $R^2$ together with the carbon atom to which they are bonded, represent saturated or unsaturated cycloalkyl or heterocyclyl having in each case 3 to 12 carbon atoms and, where appropriate, 1 to 3 identical or different heteroatoms—in particular nitrogen, oxygen and/or sulphur, which are in each case optionally substituted identically or differently once or more than once, where suitable substituents in each case are:

Halogen, straight-chain or branched alkyl having 1 to 6 carbon atoms, straight-chain or branched alkanoyl having 1 to 7 carbon atoms, straight-chain or branched alkanediyl having 3 to 8 carbon atoms, straight-chain or branched dioxyalkylene having 1 to 8 carbon atoms, straight-chain or branched halogeno-alkyl having 1 to 6 carbon atoms and 1 to 13 identical or different halogen atoms, straight-chain or branched alkoxy having 1 to 6 carbon atoms, straight-chain or branched alkylthio having 1 to 6 carbon atoms, cycloalkyl having 3 to 8 carbon atoms or aryl having 6 to 10 carbon atoms, $R^3$ represents fluorine, chlorine, bromine, iodine, straight-chain or branched alkyl having 1 to 8 carbon atoms, or straight-chain branched alkoxy having 1 to 8 carbon atoms, $R^4$ represents hydrogen, fluorine, chlorine, bromine, iodine, straight-chain or branched alkyl having 1 to 8 carbon atoms, straight-chain or branched halogenoalkyl having 1 to 8 carbon atoms and 1 to 17 identical or different halogen atoms, or straight-chain or branched alkoxy having 1 to 8 carbon atoms, $R^5$ represents fluorine, chlorine, bromine, iodine, straight-chain or branched alkyl having 1 to 8 carbon atoms, or straight-chain or branched alkoxy having 1 to 8 carbon atoms, and n represents a number 0, 1, 2 or 3.

Compounds of the formula (I) are particularly preferred in which $R^1$ represents hydrogen, in each case straight-chain or branched alkyl having 1 to 10 carbon atoms, alkenyl having 3 to 6 carbon atoms, halogenoalkyl having 1 to 6 carbon atoms and 1 to 13 identical or different halogen atoms, alkoxyalkyl having in each case 1 to 6 carbon atoms in the individual alkyl moieties, alkoxyalkoxyalkyl having in each case 1 to 6 carbon atoms in the individual alkyl moieties, alkylthioalkyl having in each case 1 to 6 carbon atoms in the individual alkyl moieties, cycloalkyl having 3 to 7 carbon atoms, saturated heterocyclyl having 3 to 7 ring members and 1 or 2 identical or different heteroatoms—in particular nitrogen, oxygen and/or sulphur—or represents arylalkyl or aryl, in each case having 6 or 10 carbon atoms in the aryl moiety and, where appropriate, 1 to 4 carbon atoms in the straight-chain or branched alkyl moiety, or heteroaryl, having 2 to 9 carbon atoms and 1 to 3 identical or different heteroatoms—in particular nitrogen, oxygen and/or sulphur, which are in each case optionally substituted identically or differently once to five times in the aryl or heteroaryl moiety, where suitable aryl or heteroaryl substituents in each case are:

halogen, nitro, in each case straight-chain or branched alkyl, alkoxy, alkylthio, alkylsulphinyl or alkylsulphonyl having in each case 1 to 4 carbon atoms, as well as in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, and $R^2$ represents hydrogen, straight-chain or branched alkyl having 1 to 10 carbon atoms, halogenoalkyl having 1 to 6 carbon atoms and 1 to 13 identical or different halogen atoms, or alkoxyalkyl having in each case 1 to 6 carbon atoms in the individual alkyl moieties, or $R^1$ and $R^2$, together with the carbon atom to which they are bonded, represent saturated or unsaturated cycloalkyl or heterocyclyl having in each case 3 to 8 carbon atoms and, where appropriate, or 1 or 2 identical or different heteroatoms—in particular nitrogen, oxygen and/or sulphur, which are in each case, where appropriate, substituted identically or differently once to four times, where suitable substituents in each case are:

fluorine, chlorine, bromine, straight-chain or branched alkyl having 1 to 4 carbon atoms, straight-chain or branched alkanoyl having 1 to 5 carbon atoms, straight-chain or branched alkanediyl having 3 to 6 carbon atoms, straight-chain or branched dioxyalkylene having 1 to 6 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched alkylthio having 1 to 4 carbon atoms, cycloalkyl having 3 to 7 carbon atoms, or phenyl, $R^3$ represents fluorine, chlorine, bromine, straight-chain or branched alkyl having 1 to 6 carbon atoms, or straight-chain or branched alkoxy having 1 to 6 carbon atoms, $R^4$ represents hydrogen, fluorine, chlorine, bromine, straight-chain or branched alkyl having 1 to 6 carbon atoms, straight-chain or branched halogenoalkyl having 1 to 6 carbon atoms and 1 to 13 identical or different halogen atoms, or straight-chain or branched alkoxy having 1 to 6 carbon atoms, $R^5$ represents fluorine, chlorine, bromine, straight-chain or branched alkyl having 1 to 6 carbon atoms, or straight-chain or branched alkoxy having 1 to 6 carbon atoms, and n represents a number 0, 1 or 2.

Compounds of the formula (I) are very particularly preferred in which $R^1$ represents hydrogen, in each case straight-chain or branched alkyl having 1 to 8 carbon atoms, alkenyl having 3 to 5 carbon atoms, halogenoalkyl having 1 to 4 carbon atoms and 1 to 9 identical or different halogen atoms, alkoxyalkyl having in each case 1 to 3 carbon atoms in the individual alkyl moieties, alkoxyalkoxyalkyl having in each case 1 to 3 carbon atoms in the individual alkyl moieties, alkylthioalkyl having in each case 1 to 3 carbon atoms in the individual alkyl moieties, cycloalkyl having 3 to 6 carbon atoms, saturated heterocyclyl having 3, 5 or 6 ring members and 1 heteroatom—in particular nitrogen, oxygen or sulphur—or represents phenylalkyl or phenyl, having optionally 1 to 3 carbon atoms in the alkyl moiety, or heteroaryl—in particular pyridyl, imidazolyl, pyrazolyl, triazolyl or thiazolyl, which are in each case optionally substituted identically or differently once to three times in the phenyl or heteroaryl moiety, where suitable phenyl or heteroaryl substituents in each case are:

fluorine, chlorine, bromine, nitro, methyl, ethyl, n- or i-propyl, n-, i-, s- or t-butyl, methoxy, ethoxy, n-, or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl or trifluoromethylsulphonyl, $R^2$ represents hydrogen, in each case straight-chain or branched alkyl having 1 to 6 carbon atoms, halogeno-alkyl having 1 to 4 carbon atoms and 1 to 9 identical or different halogen atoms, or alkoxyalkyl having in each case 1 to 4 carbon atoms in the individual alkyl moieties, or $R^1$ and $R^2$, together with the carbon atom to which they are bonded, represent saturated or unsaturated cycloalkyl or heterocyclyl in each case having 3, 5, 6, 7 or 8 carbon atoms and, where appropriate, 1 or 2 identical or different heteroatoms—in particular nitrogen, oxygen and/or sulphur, which are optionally substituted identically or differently once to three times, where in each case suitable substituents are:

fluorine, chlorine, bromine, straight-chain or branched alkyl having 1 to 4 carbon atoms, straight-chain or branched alkanoyl having 1 to 4 carbon atoms, dioxyalkylene having 1 to 3 carbon atoms, halogenoalkylene having 1 or 2 carbon atoms and 1 to 5 identical or different halogen atoms, straight-chain or branched alkoxy having 1 or 2 carbon atoms, straight-chain or branched alkylthio having 1 or 2 carbon atoms, cycloalkyl having 3, 5 or 6 carbon atoms, or phenyl, $R^3$ represents fluorine, chlorine, bromine, straight-chain or branched alkyl having 1 to 4 carbon atoms, or straight-chain or branched alkoxy having 1 to 3 carbon atoms, $R^4$ represents hydrogen, fluorine, chlorine, bromine, straight-chain or branched alkyl having 1 to 4 carbon atoms, halogenoalkyl having 1 or 2 carbon atoms and 1 to 5 identical or different halogen atoms, or straight-chain or branched alkoxy having 1 to 3 carbon atoms, $R^5$ represents fluorine, chlorine, bromine, straight-chain or branched alkyl having 1 to 4 carbon atoms, or straight-chain or branched alkoxy having 1 to 3 carbon atoms, and n represents a number 0 or 1.

Reference may specifically be made to the compounds named as preparation examples.

If, for example, 2-amino-2-methyl-butyronitrile and 2-(2, 4-dichlorophenyl)-acetyl chloride are used as the starting compounds, the course of the reaction of the process according to the invention can then be depicted by the following formula scheme:

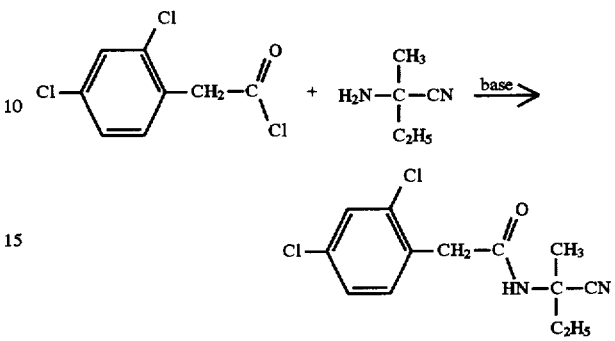

The α-amino nitriles which are required as starting compounds for carrying out the process according to the invention are generally defined by the formula (II). In this formula (II), $R^1$ and $R^2$ preferably represent those radicals which have already been mentioned, in connection with the description of the compounds of the formula (I) according to the invention, as being preferred for these substituents. The α-amino nitriles of the formula (II) are known or can be obtained by analogy with known processes (cf., e.g., U.S. Pat. No. 4,041,045; Liebigs Ann. Chem. 764, 69–93 [1972]; EP 427 907; U.S. Pat. No. 4,041,045; U.S. Pat. No. 3,422, 132; Can. J. Chem. 53, 3339–3350 [1975]; J. Amer. Chem. Soc. 94, 968–972 [1972]).

The phenylacetyl halides which are additionally required as starting compounds for carrying out the process according to the invention are generally defined by the formula (III). In this formula (III), $R^3$, $R^4$, $R^5$ and n preferably represent those radicals and indices which have already been mentioned, in connection with the description of the compounds of the formula (I) according to the invention, as being preferred for these substituents and this index. Hal preferably represents fluorine, chlorine, bromine or iodine, in particular chlorine or bromine.

The phenylacetyl halides of the formula (III) are well-known or can be obtained by analogy with known processes (cf., e.g., J. Amer. Chem. Soc. 95, 3340 [1973]).

Inert organic solvents are suitable diluents for carrying out the process according to the invention. These include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbontetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, or sulphoxides, such as dimethyl sulphoxide or sulpholane.

The process according to the invention is preferably carried out in the presence of a suitable reaction aid. All customary inorganic or organic bases are suitable as such. These include, for example, hydroxides, acetates, carbonates or hydrogen carbonates of alkaline earth metals or alkali metals, such as, for example, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, as well as, in particular, tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). It is also possible simultaneously to employ the α-amino nitrile of the formula (II) which is used as reactant, in an appropriate excess as the acid-binding agent.

In carrying out the process according to the invention, the reaction temperatures may be varied over a relatively wide range. In general, temperatures of between –20° C. and 150° C., preferably temperatures of between 0° C. and 120° C., are employed.

The process according to the invention is normally carried out under atmospheric pressure. However, it is also possible to employ increased or reduced pressure.

For carrying out the process according to the invention, 0.1 to 5.0 mol, preferably 0.5 to 2.0 mol, of phenylacetyl halide of the formula (III) and optionally 0.5 to 3.0 mol, preferably 1.0 to 2.0 mol, of reaction aid are generally employed per mol of α-amino nitrile of the formula (II). Implementation of the reaction and working up and isolation of the reaction products take place by analogy with known processes (in this connection, cf., for example, J. Org. Chem. 43, 2576–2581 [1978] or the preparation examples).

The N-phenylacetamino nitriles of the formula (I) according to the invention are suitable intermediates for preparing insecticidal, acaricidal and herbicidal 3-aryl-pyrrolidine-2, 4-diones of the formula (VI),

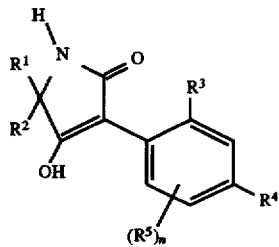

(VI)

in which

R¹, R², R³, R⁴, R⁵ and n have the abovementioned meaning, by initially reacting them in a first stage with alcohols of the formula (IV),

 R—OH (IV)

in which

R represents alkyl, optionally in the presence of a diluent and optionally in the presence of sulphuric acid as a reaction aid, and then cyclising the N-phenylacetamino carboxylic acid esters of the formula (V) thereby obtained,

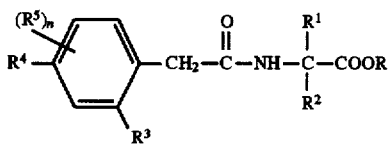

(V)

in which

R, R¹, R², R³, R⁴, R⁵ and n have the abovementioned meaning, in a subsequent second stage, optionally in the presence of a diluent and optionally in the presence of a reaction aid.

If, for example, 2-(2,4-dichlorophenyl)-N-(1-cyano-2-butyl)-acetamide and methanol are used as the starting compounds, the course of the further reaction of the compounds of the formula (I) according to the invention can then be depicted by the following formula scheme:

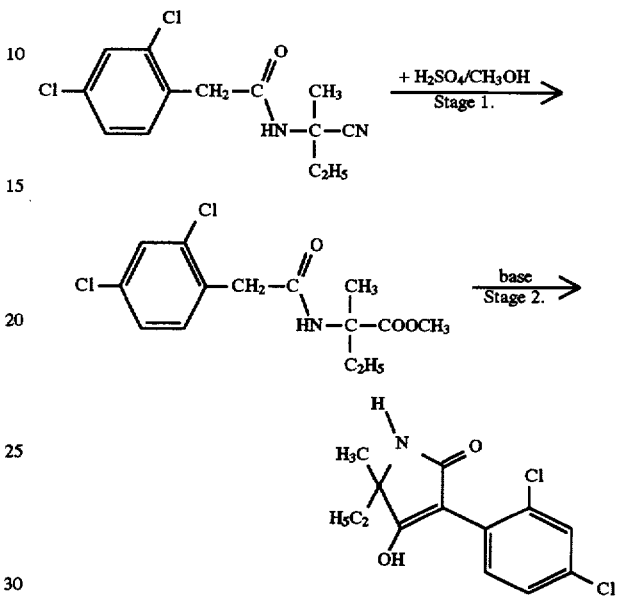

The alcohols which are required as starting compounds for carrying out the further reaction of the compounds of the formula (I) according to the invention are generally defined by the formula (IV). In this formula (IV), R preferably represents straight-chain or branched alkyl having 1 to 6, in particular 1 to 4, carbon atoms, particularly preferably methyl or ethyl. The alcohols of the formula (IV) are well known compounds in organic chemistry.

Concentrated sulphuric acid, in particular, is a suitable reaction aid for carrying out the first stage of the further reaction of the compounds of the formula (I) according to the invention. Where appropriate, it is also possible to use strongly acidic organic acids, such as, for example, phenyl-sulphonic acid, toluenesulphonic acid, methanesulphonic acid or trifluoroacetic acid.

Inert organic solvents are suitable diluents for carrying out the first stage of the further reaction of the compounds of the formula (I) according to the invention. These include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbontetrachloride, or ethers, such as diethyl ether, diisopropyl ether, dioxane, tetrahydrofuran or ethylene glycol dimethyl ether or ethylene glycol diethyl ether.

The first stage of the further reaction of the compounds of the formula (I) according to the invention is normally carried out under atmospheric pressure. However, it is also possible to employ elevated or reduced pressure.

In carrying out the first stage of the further reaction of the compounds of the formula (I) according to the invention, the reaction temperatures can be varied over a relatively wide range. In general, temperatures of between 20° C. and 150° C., preferably temperatures of between 0° C. and 120° C., are employed.

For carrying out the first stage of the further reaction of the compounds of the formula (I) according to the invention, 1.0 to 5.0 mol, preferably 1.0 to 2.5 mol, of alcohol of the formula (IV) and optionally 1.0 to 5.0 mol, preferably 1.0 to 2.5 mol, of an acid used as a reaction aid are generally employed per mol of N-phenylacetimino nitrile of the formula (I). Implementation of the reaction and working up and isolation of the reaction products takes place by analogy with known processes (in this context, cf. the preparation examples as well).

The N-phenylacetamino carboxylic acid esters of the formula (V) which can be obtained with the aid of the first stage of the further reaction of the compounds of the formula (I) according to the invention are known in some cases (cf., e.g., EP 456 063; JP 49011415).

N-phenylacetamino carboxylic acid esters of the formula (Va),

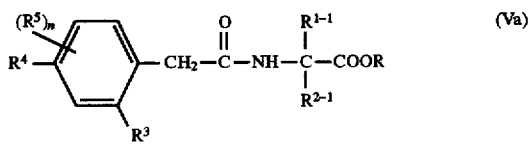

in which

R represents alkyl, $R^{1-1}$ represents hydrogen, or represents alkyl, alkenyl, cycloalkyl, aryl or heterocyclyl, which are in each case optionally substituted, and $R^{2-1}$ represents halogenoalkyl, or $R^{1-1}$ and $R^{2-1}$, together with the carbon atom to which they are bonded, represent in each case substituted cycloalkyl or heterocyclyl, and $R^3$ represents halogen, alkyl or alkoxy, $R^4$ represents hydrogen, halogen, alkyl, halogenoalkyl or alkoxy, $R^5$ represents halogen, alkyl or alkoxy, and n represents a number 0, 1, 2 or 3, are not yet known and are likewise a subject of the invention.

Compounds of the formula (Va) are preferred in which

R represents in each case straight-chain or branched alkyl having 1 to 6 carbon atoms;

$R^{1-1}$ represents hydrogen, in each case straight-chain or branched alkyl having 1 to 12 carbon atoms, alkenyl having 3 to 8 carbon atoms, halogenoalkyl having 1 to 8 carbon atoms and 1 to 17 identical or different halogen atoms, alkoxyalkyl having in each case 1 to 8 carbon atoms in the individual alkyl moieties, alkoxyalkoxylalkyl having in each case 1 to 8 carbon atoms in the individual alkyl moieties, alkylthioalkyl having in each case 1 to 8 carbon atoms in the individual alkyl moieties, cycloalkyl having 3 to 8 carbon atoms, saturated heterocyclyl having 3 to 8 ring members and 1 to 3 identical or different heteroatoms—in particular nitrogen, oxygen and/or sulphur—or represents arylalkyl or aryl, having in each case 6 to 10 carbon atoms in the aryl moiety and, where appropriate, 1 to 6 carbon atoms in the straight-chain or branched alkyl moiety, or heteroaryl, having 2 to 9 carbon atoms and 1 to 4 identical or different heteroatoms—in particular nitrogen, oxygen and/or sulphur, which are in each case optionally substituted identically or differently once or more than once in the aryl or heteroaryl moiety, where suitable aryl or heteroaryl substituents in each case are: halogen, nitro, in each case straight-chain or branched alkyl, alkoxy, alkylthio, alkylsulphinyl or alkylsulphonyl having in each case 1 to 6 carbon atoms, as well as in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, and $R^{2-1}$ represents halogenoalkyl having 1 to 8 carbon atoms and 1 to 17 identical or different halogen atoms, or $R^{1-1}$ and $R^{2-1}$, together with the carbon atom to which they are bonded, represent saturated or unsaturated cycloalkyl or heterocyclyl having 3 to 12 carbon atoms and, where appropriate, 1 to 3 identical or different heteroatoms—in particular nitrogen, oxygen and/or sulphur, which are in each case substituted identically or differently once or more than once, where suitable substituents in each case are:

halogen, straight-chain or branched alkyl having 1 to 6 carbon atoms, straight-chain or branched alkanediyl having 3 to 8 carbon atoms, straight-chain or branched dioxyalkylene having 1 to 8 carbon atoms, straight-chain or branched halogenoalkyl having 1 to 6 carbon atoms and 1 to 13 identical or different halogen atoms, straight-chain or branched alkoxy having 1 to 6 carbon atoms, straight-chain or branched alkylthio having 1 to 6 carbon atoms, cycloalkyl having 3 to 8 carbon atoms or aryl having 6 to 10 carbon atoms, $R^3$ represents fluorine, chlorine, bromine, iodine, straight-chain or branched alkyl having 1 to 8 carbon atoms, or straight-chain or branched alkoxy having 1 to 8 carbon atoms, $R^4$ represents hydrogen, fluorine, chlorine, bromine, iodine, straight-chain or branched alkyl having 1 to 8 carbon atoms, straight-chain or branched halogenoalkyl having 1 to 8 carbon atoms and 1 to 17 identical or different halogen atoms, or straight-chain or branched alkoxyhaving 1 to 8 carbon atoms, $R^5$ represents fluorine, chlorine, bromine, iodine, straight-chain or branched alkyl having 1 to 8 carbon atoms, or straight-chain or branched alkoxy having 1 to 8 carbon atoms, and n represents a number 0, 1, 2 or 3.

Compounds of the formula (Va) are particularly preferred in which

R represents in each case straight-chain or branched alkyl having 1 to 4 carbon atoms;

$R^{1-1}$ represents hydrogen, in each case straight-chain or branched alkyl having 1 to 10 carbon atoms, alkenyl having 3 to 6 carbon atoms, halogenoalkyl having 1 to 6 carbon atoms and 1 to 13 identical or different halogen atoms, alkoxyalkyl having in each case 1 to 6 carbon atoms in the individual alkyl moieties, alkoxyalkoxylalkyl having in each case 1 to 6 carbon atoms in the individual alkyl moieties, alkylthioalkyl having in each case 1 to 6 carbon atoms in the individual alkyl moieties, cycloalkyl having 3 to 7 carbon atoms, saturated heterocyclyl having 3 to 7 ring members and one or two identical or different heteroatoms—in particular nitrogen, oxygen and/or sulphur—or represents arylalkyl or aryl, having in each case 6 or 10 carbon atoms in the aryl moiety and, where appropriate, 1 to 4 carbon atoms in the straight-chain or branched alkyl moiety, or heteroaryl having 2 to 9 carbon atoms and 1 to 3 identical or different heteroatoms—in particular nitrogen, oxygen and/or sulphur, which are in each case optionally substituted identically or differently once to five times in the aryl or heteroaryl moiety, where suitable aryl or heteroaryl substituents are in each case:

halogen, nitro, in each case straight-chain or branched alkyl, alkoxy, alkylthio, alkylsulphinyl or alkylsulphonyl having in each case 1 to 4 carbon atoms, as well as in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, and $R^{2-1}$ represents halogenoalkyl having 1 to 6 carbon atoms and 1 to 13 identical or different halogen atoms, or $R^{1-1}$ and $R^{2-1}$, together with the carbon atom to which they are bonded, represent saturated or unsaturated cycloalkyl or heterocyclyl having 3 to 8 carbon atoms and, where appropriate, 1 or 2 identical or different heteroatoms—in particular nitrogen, oxygen and/or sulphur, which are in each case substituted identically or differently once to four times, where suitable substituents in each case are:

fluorine, chlorine, bromine, straight-chain or branched alkyl having 1 to 4 carbon atoms, straight-chain or branched alkanediyl having 3 to 6 carbon atoms, straight-chain or branched dioxyalkylene having 1 to 6 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched alkylthio having 1 to 4 carbon atoms, cycloalkyl having 3 to 7 carbon atoms, or phenyl, $R^3$ represents fluorine, chlorine, bromine, straight-chain or branched alkyl having 1 to 6 carbon atoms, or straight-chain or branched alkoxy having 1 to 6 carbon atoms, $R^4$ represents hydrogen, fluorine, chlorine, bromine, straight-chain or branched alkyl having 1 to 6 carbon atoms, straight-chain or branched halogenoalkyl having 1 to 6 carbon atoms and 1 to 13 identical or different halogen atoms, or straight-chain or branched alkoxy having 1 to 6 carbon atoms, $R^5$ represents fluorine, chlorine, bromine, straight-chain or branched alkyl having 1 to 6 carbon atoms, or straight-chain or branched alkoxy having 1 to 6 carbon atoms, and n represents a number 0, 1 or 2.

Compounds of the formula (Va) are very particularly preferred in which

R represents ethyl, methyl, propyl, iso-propyl;

$R^{1-1}$ represents hydrogen, in each case straight-chain or branched alkyl having 1 to 8 carbon atoms, alkenyl having 3 to 5 carbon atoms, halogenoalkyl having 1 to 4 carbon atoms and 1 to 9 identical or different halogen atoms, alkoxyalkyl having in each case 1 to 3 carbon atoms in the individual alkyl moieties, alkoxyalkoxyalkyl having in each case 1 to 3 carbon atoms in the individual alkyl moieties, alkylthioalkyl having in each case 1 to 3 carbon atoms in the individual alkyl moieties, cycloalkyl having 3 to 6 carbon atoms, saturated heterocyclyl having 3, 5 or 6 ring members and 1 heteroatom—in particular nitrogen, oxygen or sulphur—or represents phenylalkyl or phenyl, having optionally 1 to 3 carbon atoms in the alkyl moiety, or heteroaryl in particular pyridyl, imidazolyl, pyrazolyl, triazolyl or thiazolyl, which are in each case optionally substituted identically or differently once to three times in the phenyl or heteroaryl moiety, where suitable phenyl or heteroaryl substituents in each case are:

fluorine, chlorine, bromine, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl or trifluoromethylsulphonyl, $R^{2-1}$ represents halogenoalkyl having 1 to 4 carbon atoms and 1 to 9 identical or different halogen atoms, or $R^{1-1}$ and $R^{2-1}$, together with the carbon atom to which they are bonded, represent saturated or unsaturated cycloalkyl having 3, 5, 6, 7 or 8 carbon atoms, which is substituted identically or differently once to three times, where suitable substituents are:

fluorine, chlorine, bromine, straight-chain or branched alkyl having 1 to 4 carbon atoms, halogenoalkyl having 1 or 2 carbon atoms and 1 to 5 identical or different halogen atoms, straight-chain or branched alkoxy having 1 or 2 carbon atoms, straight-chain or branched alkylthio having 1 or 2 carbon atoms, cycloalkyl having 3, 5 or 6 carbon atoms, or phenyl, $R^3$ represents fluorine, chlorine, bromine, straight-chain or branched alkyl having 1 to 4 carbon atoms, or straight-chain or branched alkoxy having 1 to 3 carbon atoms, $R^4$ represents hydrogen, fluorine, chlorine, bromine, straight-chain or branched alkyl having 1 to 4 carbon atoms, halogenoalkyl having 1 or 2 carbon atoms and 1 to 5 identical or different halogen atoms, or straight-chain or branched alkoxy having 1 to 3 carbon atoms, $R^5$ represents fluorine, chlorine, bromine, straight-chain or branched alkyl having 1 to 4 carbon atoms, or straight-chain or branched alkoxy 1 to 3 carbon atoms, and n represents a number 0 or 1.

Inert organic solvents are suitable diluents for carrying out the second stage of the further reaction of the compounds of the formula (I) according to the invention. These include, in particular, aliphatic, alicyclic or aromatic, optionally halogenated hydrocarbons, such as, for example, benzine, benzene, toluene, xylene, chlorobenzene, dichlorobenzene, petroleum ether, hexane or cyclohexane, ethers, such as diethyl ether, diisopropyl ether, dioxane, tetrahydrofuran or ethylene glycol dimethyl ether or ethylene glycol diethyl ether; amides, such as N,N-dimethylformamide, N,N-dimethylacetamide, N-methylformanilide, N-methylpyrrolidone or hexamethylphosphoric triamide; sulphoxides, such as dimethyl sulphoxide or sulpholane, or alcohols, such as methanol, ethanol, n- or i-propanol, ethylene glycol monomethyl ether, ethylene glycol monoethyl ether, diethylene glycol monomethyl ether or diethylene glycol monoethyl ether.

The second stage of the further reaction of the compounds of the formula (I) according to the invention is preferably carried out in the presence of a suitable reaction aid. All customary inorganic or organic bases are suitable as such. These include, for example, hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The second stage of the further reaction of the compounds of the formula (I) according to the invention can optionally be carried out in a two-phase system, such as, for example, water/toluene or water/dichloromethane, optionally in the presence of a suitable phase transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyldimethyl-ammonium methyl sulphate, dimethyl-$C_{12}/C_{14}$-alkyl-benzylammonium chloride, dimethyl-$C_{12}/$ $C_{14}$-alkyl-benzylammonium bromide and methyl-trialkyl-$C_8/C_{10}$-ammonium chloride; tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

The second stage of the further reaction of the compounds of the formula (I) according to the invention is normally carried out under atmospheric pressure. However, it is also possible to employ elevated or reduced pressure.

In carrying out the second stage of the further reaction of the compounds of the formula (I) according to the invention, the reaction temperatures may be varied over a relatively wide range. In general, temperatures of between 0° C. and 250° C., preferably temperatures of between 20° C. and 200° C., are employed.

For carrying out the second stage of the further reaction of the compounds of the formula (I) according to the invention, 1.0 to 5.0 mol, preferably 1.0 to 2.5 mol, of base used as a reaction aid are generally employed per mol of N-phenylacetamino carboxylic acid ester of the formula (V).

Implementation of the reaction, and working up and isolation of the reaction products, takes place by analogy with known processes (in this context cf., for example, EP 456 063 or the preparation examples).

Purification of the intermediates and end products of the individual stages is effected using customary processes, for example by column chromatography or by recrystallisation.

Characterisation is effected using the melting point or, in the case of non-crystallising compounds, using proton nuclear magnetic resonance spectroscopy ($^1$H-NMR).

The 3-aryl-pyrrolidine-2,4-diones of the formula (VI) which can be obtained using the N-phenylacetamino nitriles of the formula (I) according to the invention and the N-phenylacetamino carboxylic acid esters of the formula (V) are either known as insecticides, acaricides and herbicides (cf., e.g., EP 456 063), or are the subject of a separate, parallel patent application.

Preparation Examples:

Example 1:

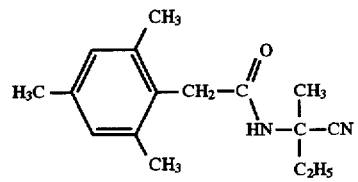

58.8 g (0.3 mol) of mesityleneacetyl chloride (cf., e.g., Tetrahedron 31, 2691–2694 [1975]) in 50 ml of absolute tetrahydrofuran are added dropwise at 0° C. to 10° C., and while stirring, to 29.4 g (0.3 mol) of 2-amino-2-methyl-butyronitrile (cf., e.g., U.S. Pat. No. 4,041,045) and 42 ml (0.3 mol) of triethylamine in 450 ml of absolute tetrahydrofuran and, once addition is complete, the mixture is stirred at room temperature until the starting compound is no longer detectable by thin layer chromatography. For the working up, the reaction mixture is added while stirring to a mixture consisting of 1000 ml of ice water and 200 ml of 1N hydrochloric acid, the precipitated solid is filtered off with suction, the residue is dissolved in dichloromethane, the aqueous phase is separated off, the organic phase is dried over magnesium sulphate, and the solvent is removed in vacuo.

69.5 g (90% of theory) of 2-(2,4,6-trimethylphenyl)-N-(2-cyano-2-butyl)-acetamide are obtained with a melting point of 155°–157° C.

The following N-phenylacetamino nitriles of the general formula (I) are obtained in a corresponding manner and in accordance with the general instructions for the preparation:

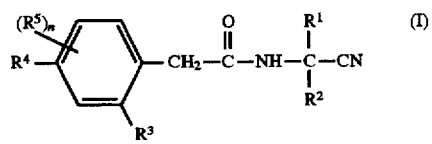

| Example no. | $R^1$ | $R^2$ | $R^3$ | Physical properties |
|---|---|---|---|---|
| 2 | $C_2H_5$ | $CH_3$ | Cl, Cl-phenyl | m.p. 141° C. |
| 3 | n-$C_3H_7$ | $CH_3$ | Cl, Cl-phenyl | m.p. 87° C. |

-continued $$\underset{R^3}{\underset{|}{\overset{(R^5)_n}{\overset{|}{R^4-}}}}\text{—}CH_2\text{—}\overset{O}{\overset{\|}{C}}\text{—}NH\text{—}\overset{R^1}{\underset{R^2}{\overset{|}{C}}}\text{—}CN \quad (I)$$

| Example no. | R¹ | R² | (R⁵)ₙ, R⁴, R³ aryl | Physical properties |
|---|---|---|---|---|
| 4 | i-C₃H₇ | CH₃ | 2,4-diCl-phenyl | m.p. 132° C. |
| 5 | i-C₄H₉ | CH₃ | 2,4-diCl-phenyl | m.p. 110° C. |
| 6 | cyclopropyl | CH₃ | 2,4-diCl-phenyl | m.p. 124° C. |
| 7 | —CH(CH₃)—(CH₂)₄— | | 2,4-diCl-phenyl | m.p. 153° C. |
| 8 | —CH₂—CH(CH₃)—(CH₂)₃— | | 2,4-diCl-phenyl | m.p. 189° C. |
| 9 | —(CH₂)₂—CH(CH₃)—(CH₂)₂— | | 2,4-diCl-phenyl | m.p. 203° C. |
| 10 | —CH₂—CH(CH₃)—CH(CH₃)—(CH₂)₂— | | 2,4-diCl-phenyl | m.p. 153° C. |
| 11 | i-C₃H₇ | CH₃ | 2,4-diCH₃-phenyl | m.p. 128° C. |
| 12 | —(CH₂)₂—CH(CH₃)—(CH₂)₂— | | 2,4-diCH₃-phenyl | m.p. 198° C. |

-continued $$\underset{R^3}{\underset{R^4\underset{}{\overset{(R^5)_n}{\diagdown}}}{\diagdown}}CH_2-\overset{O}{\overset{\|}{C}}-NH-\underset{R^2}{\overset{R^1}{\overset{|}{C}}}-CN \quad (I)$$

| Example no. | R¹ | R² | $\underset{R^3}{\underset{R^4\underset{}{\overset{(R^5)_n}{\diagdown}}}{\diagdown}}$ | Physical properties |
|---|---|---|---|---|
| 13 | CH₃ | CH₃ | 2,4,5-tri(CH₃)-phenyl | m.p. 212–215° C. |
| 14 | n-C₃H₇ | CH₃ | 2,4,5-tri(CH₃)-phenyl | m.p. 153–155° C. |
| 15 | i-C₃H₇ | CH₃ | 2,4,5-tri(CH₃)-phenyl | m.p. 126–128° C. |
| 16 | i-C₄H₉ | CH₃ | 2,4,5-tri(CH₃)-phenyl | m.p. 152–153° C. |
| 17 | t-C₄H₉ | CH₃ | 2,4,5-tri(CH₃)-phenyl | m.p. 138–140° C. |
| 18 | C₂H₅ | C₂H₅ | 2,4,5-tri(CH₃)-phenyl | m.p. 139–140° C. |
| 19 | cyclopropyl | CH₃ | 2,4,5-tri(CH₃)-phenyl | m.p. 137° C. |

-continued
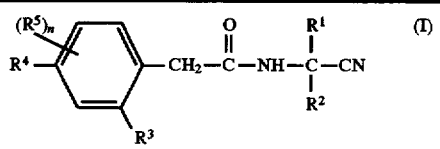
| Example no. | R¹ | R² | 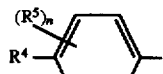 R³ | Physical properties |
|---|---|---|---|---|
| 20 | CH₃–CF(CH₃)– (F-C with two CH₃) | CH₃ | 2,4,6-tri(CH₃) phenyl | m.p. 112° C. |
| 21 | CF₃ | CH₃ | 2,4,6-tri(CH₃) phenyl | m.p. 184° C. |
| 22 | $C_2H_5-S-CH_2-$ | CH₃ | 2,4,6-tri(CH₃) phenyl | m.p. 115° C. |
| 23 | $-CH(CH_3)-(CH_2)_4-$ | | 2,4,6-tri(CH₃) phenyl | m.p. 183–184° C. |
| 24 | $-CH_2-CH(CH_3)-(CH_2)_3-$ | | 2,4,6-tri(CH₃) phenyl | m.p. 176° C. |
| 25 | $-(CH_2)_2-CH(CH_3)-(CH_2)_2-$ | | 2,4,6-tri(CH₃) phenyl | m.p. 202° C. |
| 26 | $-CH_2-CH(CH_3)-CH(CH_3)-(CH_2)_2-$ | | 2,4,6-tri(CH₃) phenyl | m.p. 174° C. |

-continued $$\text{(R}^5\text{)}_n\text{-Ar-CH}_2\text{-C(=O)-NH-C(R}^1\text{)(R}^2\text{)-CN} \quad (I)$$

where the aryl bears $R^4$, $R^3$, $(R^5)_n$ substituents.

| Example no. | R¹ R² | (R⁵)ₙ / R⁴ / R³ aryl | Physical properties |
|---|---|---|---|
| 27 | —(CH₂)₂—CH(i-C₃H₇)—(CH₂)₂— | 2,4,5-tri-CH₃-phenyl | m.p. 204–206° C. |
| 28 | —(CH₂)₆— | 2,4,5-tri-CH₃-phenyl | m.p. 173° C. |
| 29 | —(CH₂)₆— | 2,4-di-Cl-phenyl | m.p. 184° C. |
| 30 | —(CH₂)₂—CH(C₂H₅)—(CH₂)₂— | 2,4,5-tri-CH₃-phenyl | m.p. 185° C. |
| 31 | —(CH₂)₂—CH(C₂H₅)—(CH₂)₂— | 2,4-di-Cl-phenyl | m.p. 194° C. |
| 32 | —CH₂—S—(CH₂)₂— | 2,4,5-tri-CH₃-phenyl | m.p. 174–175° C. |
| 33 | —(CH₂)₂—C(OCH₂CH₂O)—(CH₂)₂— (spiro dioxolane) | 2,4,5-tri-CH₃-phenyl | m.p. >220° C. |

-continued
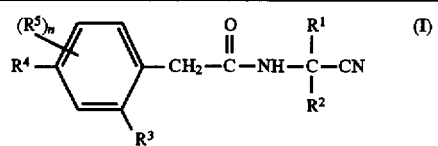
| Example no. | R¹ | R² | 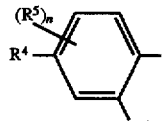 R³ | Physical properties |
|---|---|---|---|---|
| 34 | | —(CH$_2$)$_2$—C(CH$_3$)$_2$—(CH$_2$)$_2$— | 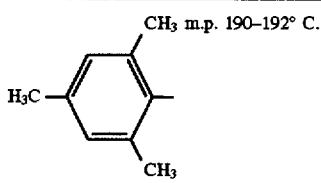 | m.p. 190–192° C. |
| 35 | | —CH$_2$—S—(CH$_2$)$_2$— | 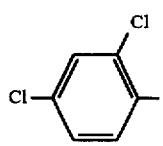 | m.p. 131–133° C. |
| 36 | | —(CH$_2$)$_2$—CH(OCH$_3$)—(CH$_2$)$_2$— | 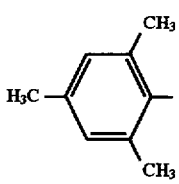 | m.p. 159–160° C. |
| 37 | 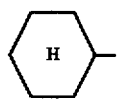 | CH$_3$ | 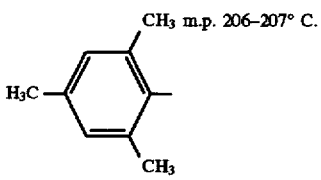 | m.p. 206–207° C. |
| 38 | | —(CH$_2$)$_2$—N(CH$_3$)—(CH$_2$)$_2$— | 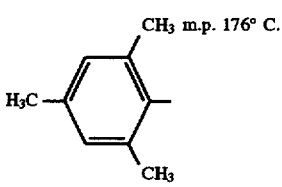 | m.p. 176° C. |
| 39 | | 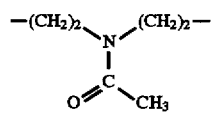 | 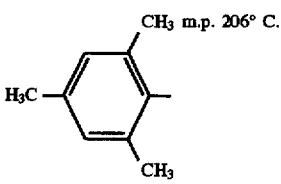 | m.p. 206° C. |
| 40 | | —(CH$_2$)$_2$—CH(CH$_3$)—CH$_2$— | 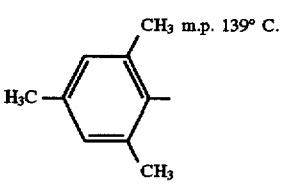 | m.p. 139° C. |

-continued
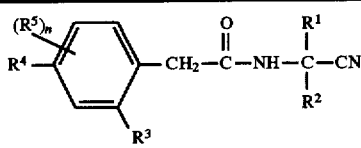
| Example no. | R¹ | R² | (R⁵)ₙ, R⁴, R³ aryl | Physical properties |
|---|---|---|---|---|
| 41 | | —(CH₂)₃—CH(CH₃)— | 2,4,5-tri-CH₃ phenyl | m.p. 142° C. |
| 42 | | —(CH₂)₂\_CH(cyclohexyl)\_(CH₂)₂— | 2,4,5-tri-CH₃ phenyl | m.p. 208° C. |
| 43 | | —(CH₂)₂\_CH(phenyl)\_(CH₂)₂— | 2,4,5-tri-CH₃ phenyl | m.p. 235–238° C. |
| 44 | | —(CH₂)₂—S—(CH₂)₂— | 2,4,5-tri-CH₃ phenyl | m.p. >220° C. |
| 45 | | —(CH₂)₂—CH(C₂H₅)—CH₂— | 2,4,5-tri-CH₃ phenyl | m.p. 185 C. |
| 46 | | —(CH₂)₂\_CH(cyclohexyl)\_(CH₂)₂— | 2,4-di-Cl phenyl | m.p. 119 C. |
| 47 | bicyclic | | 2,4,5-tri-CH₃ phenyl | m.p. 199–201 C. |

-continued
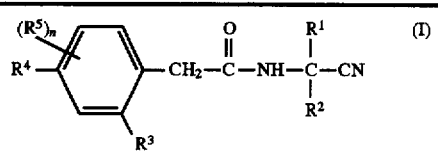
| Example no. | R¹ | R² | 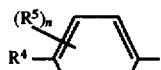 | Physical properties |
|---|---|---|---|---|
| 48 | |  | 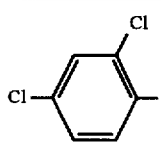 | m.p. 145–146 C. |
| 49 | |  | 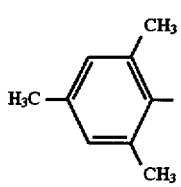 | m.p. 182–183 C. |
| 50 | |  | 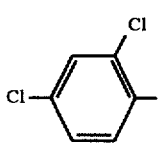 | m.p. 198–199 C. |
| 51 | s-C₄H₉ | CH₃ | 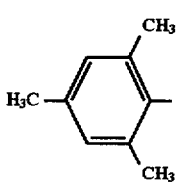 | m.p. 158–163 C. |
| 52 | s-C₄H₉ | CH₃ | 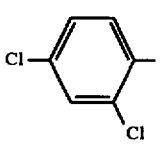 | m.p. 106–111 C. |
| 53 | i-C₃H₇ | CH₃ | 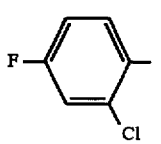 | m.p. 109–111 C. |
| 54 | i-C₃H₇ | CH₃ | 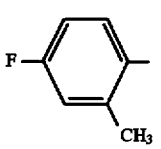 | m.p. 118–119 C. |
| 55 | i-C₃H₇—CHCH₃— | CH₃ | 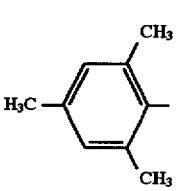 | m.p. 134–135 C. |

-continued

| Example no. | R¹ | R² | (R⁵)ₙ, R⁴, R³ | Physical properties |
|---|---|---|---|---|
| 56 | cyclopropyl | $CH_3$ | 2,5-dimethylphenyl | m.p. 112–113 C. |
| 57 | s-Bu | $CH_3$ | 2,5-dimethylphenyl | m.p. 135–141 C. |
| 58 | $-(CH_2)_2-N-(CH_2)_2-$ with benzoyl on N | | 2,4,5-trimethylphenyl ($CH_3$, $CH_3$, $CH_3$) | m.p. 120 C. |
| 59 | $-(CH_2)_2-N-(CH_2)_2-$ with $-C(O)OC_2H_5$ on N | | 2,4,5-trimethylphenyl | m.p. 161 C. |
| 60 | cyclohexane-fused (spiro) | | 2,4,5-trimethylphenyl | m.p. 147 C. |
| 61 | cyclohexane-fused (spiro) | | 2,6-dichlorophenyl (Cl, Cl) | m.p. 125 C. |

Preparation of the secondary products:

Examples V-1:

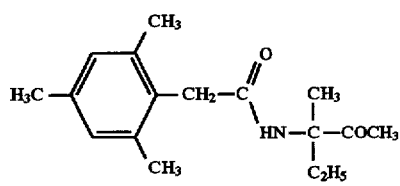

66.8 g (0.259 mol) of 2-(2,4,6-trimethylphenyl)-N-(2-cyano-2-butyl)-acetamide dissolved in 260 ml of dichloromethane are added dropwise, while stirring and cooling with ice, to 127 g (1.293 mol) of concentrated sulphuric acid, during which the temperature of the reaction mixture rises to 30° C. to 40° C., and, once addition is complete, the mixture is stirred at 30° C. to 40° C. for a further 2 hours until the dichloromethane phase of the reaction mixture has become colourless. Subsequently, while cooling with ice, 180 ml of absolute methanol are added, also dropwise, during which the reaction mixture heats once again to 40° C. Subsequently, the mixture is stirred at 40° C. to 70° C. for a further 6 hours. For the working up, the reaction mixture is added, while stirring, to 1300 g of ice, extraction is carried out with dichloromethane, the combined organic phases are washed until acid free with aqueous sodium hydrogen carbonate solution, drying is carried out over magnesium sulphate, and the solvent is removed in vacuo.

62.5 g (83% of theory) of 2-(2,4,6-trimethylphenyl)-N-(2-methoxy-carbonyl-2-butyl)acetamide are obtained with a melting point of 107°–109° C.

The following N-phenylacetamino carboxylic acid esters of the formula (V) are obtained in a corresponding manner and in accordance with the general instructions for the preparation.

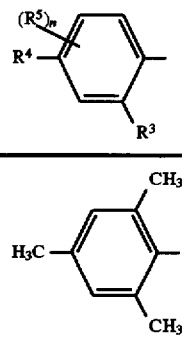

| Example no. | R | $R^1$ | $R^2$ | $R^3$ | Physical properties |
|---|---|---|---|---|---|
| V-2 | $C_2H_5$ | | $-(CH_2)_4-$ | $CH_3$ ![3,5-dimethyl] | m.p. 139° C. |
| V-3 | $CH_3$ | $CH_3$ | $CH_3$ | $CH_3$ ![3,5-dimethyl] | m.p. 140° C. |
| V-4 | $CH_3$ | | $-(CH_2)_5-$ | $CH_3$ ![3,5-dimethyl] | m.p. 104–109° C. |
| V-5 | $CH_3$ | | $-(CH_2)_4-$ | $CH_3$ ![3,5-dimethyl] | m.p. 148° C. |
| V-6 | $CH_3$ | $CH_3$ | $CH_3$ | $CH_3$ ![3-methyl] | m.p. 122–123° C. |
| V-7 | $CH_3$ | $CH_3$ | $CH_3$ | Cl ![3-chloro] | m.p. 133–134° C. |
| V-8 | $CH_3$ | | $-(CH_2)_5-$ | Cl ![3-chloro] | m.p. 108–109° C. |

-continued $$\underset{R^3}{\underset{R^4}{(R^5)_n}}\text{—}CH_2\text{—}\overset{O}{\underset{}{C}}\text{—}NH\text{—}\overset{R^1}{\underset{R^2}{C}}\text{—}COOR \quad (V)$$

| Example no. | R | R¹ | R² | (R⁵)ₙ—Ar(R⁴)(R³) | Physical properties |
|---|---|---|---|---|---|
| V-9 | $C_2H_5$ | $-CH_2-C_6H_5$ | H | R³=CH₃; R⁴=H₃C, additional CH₃ | m.p. 133° C. |
| V-10 | $CH_3$ | 2-thienyl | H | R³=CH₃; R⁴=H₃C, additional CH₃ | m.p. 146–148° C. |
| V-11 | $C_2H_5$ | $CH_2$–(4-Cl-C₆H₄) | H | R³=CH₃; R⁴=H₃C, additional CH₃ | m.p. 157–158° C. |
| V-12 | $C_2H_5$ | $CH_2$–(4-OCH₃-C₆H₄) | H | R³=CH₃; R⁴=H₃C, additional CH₃ | m.p. 118–120° C. |
| V-13 | $CH_3$ | $i\text{-}C_4H_9$ | $CH_3$ | R³=CH₃; R⁴=H₃C, additional CH₃ | m.p. 87–89° C. |
| V-14 | $CH_3$ | $C_6H_5$ | H | R³=CH₃; R⁴=H₃C, additional CH₃ | m.p. 155–156° C. |
| V-15 | $CH_3$ | $CH_3$ | $CH_3$ | R³=Cl; R⁴=F₃C, additional Cl | m.p. 163–166° C. |

-continued
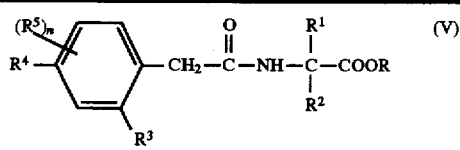
| Example no. | R | R¹ | R² | R³ | Physical properties |
|---|---|---|---|---|---|
| V-16 | $CH_3$ | $C_2H_5$ | $C_2H_5$ | $CH_3$, $H_3C$-ring-$CH_3$ | m.p. 98–101° C. |
| V-17 | $C_2H_5$ | n-$C_4H_9$ | $CH_3$ | $CH_3$, $H_3C$-ring-$CH_3$ | m.p. 110–112° C. |
| V-18 | $C_2H_5$ | i-$C_3H_7$ | $CH_3$ | $CH_3$, $H_3C$-ring-$CH_3$ | m.p. 72–74° C. |
| V-19 | $CH_3$ | $CH_3$ | H | $CH_3$, $H_3C$-ring-$CH_3$ | m.p. 130–131° C. |
| V-20 | $CH_3$ | s-$C_4H_9$ | $CH_3$ | $CH_3$, $H_3C$-ring-$CH_3$ | m.p. 88–89° C. |
| V-21 | $C_2H_5$ | i-$C_4H_9$ | $CH_3$ | $CH_3$, $H_3C$-ring-$CH_3$ | m.p. 87–88° C. |
| V-22 | $CH_3$ | —$(CH_2)_2$—$CH(CH_3)$—$(CH_2)_2$— | | $CH_3$, $H_3C$-ring-$CH_3$ | m.p. 149–151° C. (trans-isomeric) |

-continued
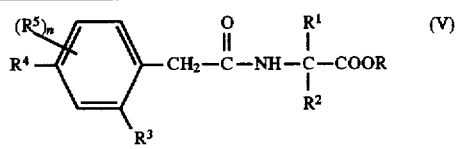
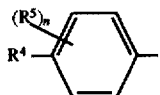
| Example no. | R | R[1] | R[2] | R[3] | Physical properties |
|---|---|---|---|---|---|
| V-23 | $CH_3$ | $-CH_2-CH(CH_3)-(CH_2)_3-$ | | 2,4,5-tri-$CH_3$ | m.p. 123–124° C. (trans-isomeric) |
| V-24 | $C_2H_5$ | 4-$C(CH_3)_3$-phenyl | H | 2-F, 4-Cl | m.p. 111° C. |
| V-25 | $CH_3$ | $CH_3$ | $CH_3$ | 2-F | m.p. 80° C. |
| V-26 | $CH_3$ | $-(CH_2)_2-CH(C(CH_3)_3)-(CH_2)_2-$ | | 2,4,5-tri-$CH_3$ | m.p. 153–154° C. |
| V-27 | $CH_3$ | $-CH(CH_3)-(CH_2)_4-$ | | 2,4,5-tri-$CH_3$ | m.p. 103–104° C. |
| V-28 | $CH_3$ | $-(CH_2)_6-$ | | 2,4,5-tri-$CH_3$ | m.p. 107–108° C. |
| V-29 | $CH_3$ | $-(CH_2)_7-$ | | 2,4,5-tri-$CH_3$ | m.p. 118–120° C. |

-continued
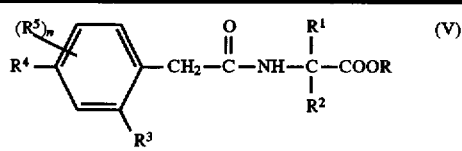
| Example no. | R | R¹ | R² | 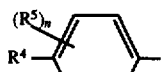 R³ | Physical properties |
|---|---|---|---|---|---|
| V-30 | $C_2H_5$ | $CH_3$ | $CH_3$ | 2,4,5-tri-$CH_3$ phenyl | |
| V-31 | $CH_3$ | $t\text{-}C_4H_9$ | $CH_3$ | 2,4,5-tri-$CH_3$ phenyl | m.p. 100° C. |
| V-32 | $CH_3$ | $CH_3$ | $CH_3$ | 2-F, 6-Cl phenyl | m.p. 121° C. |
| V-33 | $CH_3$ | $CH_3$ | $CH_3$ | 2,6-di-Cl phenyl | m.p. 145° C. |
| V-34 | $CH_3$ | $-(CH_2)_5-$ | | 2,6-di-Cl phenyl | m.p. 167–168° C. |
| V-35 | $CH_3$ | $-(CH_2)_5-$ | | 2-Cl, 6-F phenyl | m.p. 164–165° C. |
| V-36 | $CH_3$ | $C_2H_5$ | $CH_3$ | 2,4-di-Cl phenyl | m.p. 71–72° C. |

-continued

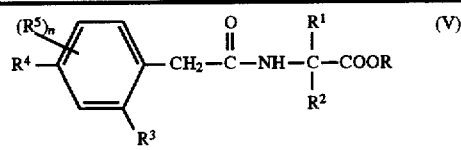

| Example no. | R | R¹ | R² | R³ with ring | Physical properties |
|---|---|---|---|---|---|
| V-37 | $CH_3$ | $i\text{-}C_3H_7$ | $CH_3$ | 2,4-dichlorophenyl | m.p. 71–72° C. |
| V-38 | $CH_3$ | $i\text{-}C_4H_9$ | $CH_3$ | 2,4-dichlorophenyl | m.p. 90° C. |
| V-39 | $CH_3$ | $-CH(CH_3)-(CH_2)_4-$ | | 2,4-dichlorophenyl | m.p. 156° C. |
| V-40 | $CH_3$ | $-(CH_2)_5-$ | | 2,6-dichloro-4-(trifluoromethyl)phenyl | m.p. 159° C. |
| V-41 | $CH_3$ | $n\text{-}C_3H_7$ | $CH_3$ | 2,4-dichlorophenyl | m.p. 96° C. |
| V-42 | $CH_3$ | cyclopropyl | $CH_3$ | 2,4,6-trimethylphenyl | m.p. 110° C. |
| V-43 | $CH_3$ | $F-C(CH_3)_2-$ | $CH_3$ | 2,4,6-trimethylphenyl | m.p. 87° C. |
| V-44 | $CH_3$ | $-(CH_2)_2-CH(CH_3)-(CH_2)_2-$ | | 2,4,6-trimethylphenyl | m.p. 146° C. (cis-isomeric) |

-continued
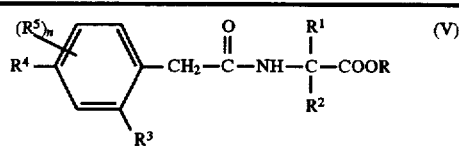
| Example no. | R | $R^1$ | $R^2$ | $R^3$ | Physical properties |
|---|---|---|---|---|---|
| V-45 | $CH_3$ | $C_2H_5-S-CH_2-$ | $CH_3$ | 2,5-di-$CH_3$, 4-$CH_3$ | m.p. 83–84° C. |
| V-46 | $CH_3$ | $CF_3$ | $CH_3$ | 2,5-di-$CH_3$, 4-$CH_3$ | m.p. 111° C. |
| V-47 | $CH_3$ | $-CH_2-CH(CH_3)-(CH_2)_3-$ | | 2-Cl, 4-Cl | m.p. 144° C. |
| V-48 | $CH_3$ | $-(CH_2)_2-CH(CH_3)-(CH_2)_2-$ | | 2-Cl, 4-Cl | m.p. 118° C. |
| V-49 | $CH_3$ | $-(CH_2)_5-$ | | 2-$CH_3$, 4-$CH_3$ | m.p. 135° C. |
| V-50 | $CH_3$ | $-(CH_2)_5-$ | | 2-Cl, 4-$F_3C$, 5-F | m.p. 151–153° C. |
| V-51 | $CH_3$ | i-$C_3H_7$ | $CH_3$ | 2-$CH_3$, 4-$CH_3$ | m.p. 79–80° C. |
| V-52 | $CH_3$ | $-(CH_2)_2-CH(CH_3)-(CH_2)_2-$ | | 2-$CH_3$, 4-$CH_3$ | m.p. 127–128° C. |

-continued

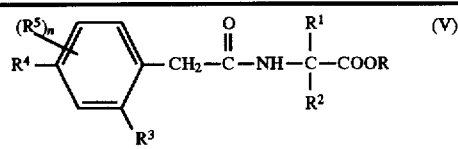

(V)

| Example no. | R | R¹ | R² | (R⁵)ₙ / R⁴ / R³ aryl | Physical properties |
|---|---|---|---|---|---|
| V-53 | $CH_3$ | $CH_3$ | $CH_3$ | 5-Cl, 2-F phenyl | m.p. 118° C. |
| V-54 | $CH_3$ | \-(CH₂)₂–CH(CH(CH₃)₂)–(CH₂)₂\- (spiro) | | 2,4,5-tri-CH₃ phenyl (with CH₃ at R³) | m.p. 137–139° C. |
| V-55 | $CH_3$ | –(CH₂)₂– (spiro) | | 2,4,5-tri-CH₃ phenyl | m.p. 181–182° C. |
| V-56 | $CH_3$ | –(CH₂)₆– (spiro) | | 2,5-di-Cl phenyl | m.p. 127–128° C. |
| V-57 | $CH_3$ | –CH₂–S–(CH₂)₂– (spiro) | | 2,4,5-tri-CH₃ phenyl | m.p. 111–113° C. |
| V-58 | $CH_3$ | –(CH₂)₂–C(CH₃)₂–(CH₂)₂– (spiro) | | 2,4,5-tri-CH₃ phenyl | m.p. 142° C. |
| V-59 | $CH_3$ | –(CH₂)₂–CH(C₂H₅)–(CH₂)₂– (spiro) | | 2,5-di-Cl phenyl | m.p. 103–105° C. |
| V-60 | $CH_3$ | –(CH₂)₂–CH(C₂H₅)–(CH₂)₂– (spiro) | | 2,4,5-tri-CH₃ phenyl | m.p. 144–145° C. (cis-isomeric) |

-continued
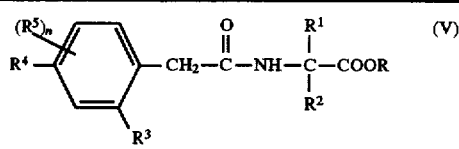
| Example no. | R | R¹ | R² | R³ | Physical properties |
|---|---|---|---|---|---|
| V-61 | $CH_3$ | $-(CH_2)_2-CH(C_2H_5)-(CH_2)_2-$ | | 2,4,5-tri-CH₃ phenyl | m.p. 129–130° C. (trans-isomeric) |
| V-62 | $CH_3$ | $-(CH_2)_2-S-(CH_2)_2-$ | | 2,4,5-tri-CH₃ phenyl | m.p. 158° C. |
| V-63 | $CH_3$ | $-(CH_2)_2-N(CH_3)-(CH_2)_2-$ | | 2,4,5-tri-CH₃ phenyl | m.p. 128–130° C. |
| V-64 | $CH_3$ | $-(CH_2)_2-N(COCH_3)-(CH_2)_2-$ | | 2,4,5-tri-CH₃ phenyl | m.p. 148–150° C. |
| V-65 | $CH_3$ | $-CH_2-S-(CH_2)_2-$ | | 2,4-di-Cl phenyl | m.p. 133–135° C. |
| V-66 | $CH_3$ | $-(CH_2)_2-CH(OCH_3)-(CH_2)_2-$ | | 2,4,5-tri-CH₃ phenyl | m.p. 116–118° C. |
| V-67 | $CH_3$ | cyclohexyl | $CH_3$ | 2,4,5-tri-CH₃ phenyl | m.p. 129–130° C. |

-continued
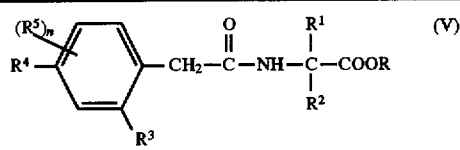
| Example no. | R | R¹ | R² | R³ | Physical properties |
|---|---|---|---|---|---|
| V-68 | $CH_3$ | \-$CH_2$-$CH(CH_3)$-$(CH_2)_2$- | | 2,4,5-tri-$CH_3$ phenyl | m.p. 83–85° C. |
| V-69 | $CH_3$ | -$CH(CH_3)$-$(CH_2)_3$- | | 2,4,5-tri-$CH_3$ phenyl | m.p. 107–108 C. |
| V-70 | $CH_3$ | -$(CH_2)_2$-CH(H-cyclohexyl)-$(CH_2)_2$- | | 2,4,5-tri-$CH_3$ phenyl | m.p. 208–210 C. |
| V-71 | $CH_3$ | -$(CH_2)_2$-CH(phenyl)-$(CH_2)_2$- | | 2,4,5-tri-$CH_3$ phenyl | m.p. 207 C. |
| V-72 | $CH_3$ | -$(CH_2)_2$-C(cyclohexyl)-$(CH_2)_2$- | | 2,4,5-tri-$CH_3$ phenyl | m.p. 153–154 C. |
| V-73 | $CH_3$ | cyclohexyl | $CH_3$ | 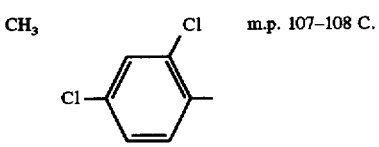 | m.p. 107–108 C. |
| V-74 | $CH_3$ | -$(CH_2)_2$-O-$(CH_2)_2$- | | 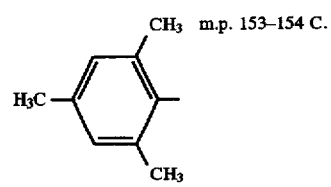 | m.p. 153–154 C. |

-continued
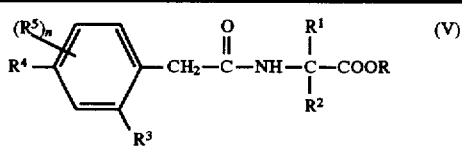
| Example no. | R | R¹ | R² |  | Physical properties |
|---|---|---|---|---|---|
| V-75 | CH₃ | —(CH₂)₂—O—(CH₂)₂— | | 2,4-Cl,Cl | m.p. 130–131 C. |
| V-76 | CH₃ | (cyclopentane ring) | | 2,4,5-tri-CH₃ | m.p. 129–131 C. |
| V-77 | CH₃ | (cyclopentane ring) | | 2,4-Cl,Cl | m.p. 136–138 C. |
| V-78 | CH₃ | s-C₄H₉ | CH₃ | 2,4,5-tri-CH₃ | m.p. 93–94 C. |
| V-79 | CH₃ | s-C₄H₉ | CH₃ | 2,4-Cl,Cl | m.p. 74–75 C. |
| V-80 | CH₃ | i-C₃H₇ | CH₃ | 2-Cl,4-F | m.p. 76–77 C. |
| V-81 | CH₃ | i-C₃H₇ | CH₃ | 2-CH₃,4-F | glassy |
| V-82 | CH₃ | (cyclopropyl) | CH₃ | 2,4-di-CH₃ | oil |

-continued
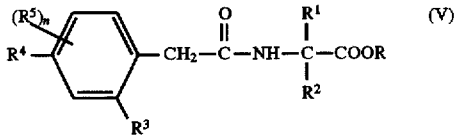
| Example no. | R | R¹ | R² | (R⁵)ₙ, R⁴, R³ | Physical properties |
|---|---|---|---|---|---|
| V-83 | $CH_3$ | s-$C_4H_9$ | $CH_3$ | 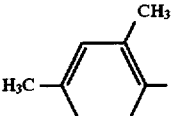 | oil |
| V-84 | $CH_3$ | i-$C_3H_7$—CHCH₃— | $CH_3$ | 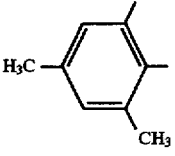 | adhesive |
| V-85 | $CH_3$ |  | | 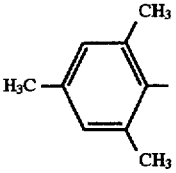 | m.p. 62–65 C. |
| V-86 | $CH_3$ | 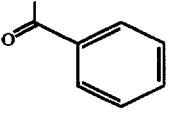 | | 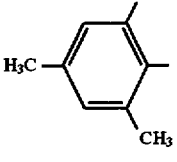 | adhesive |
| V-87 | $CH_3$ | 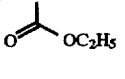 | | 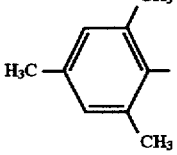 | m.p. 121 C. |
| V-88 | $CH_3$ | 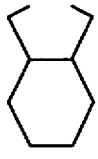 | | 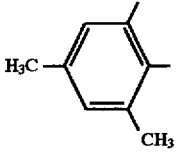 | m.p. 132 C. |
| V-89 | $CH_3$ | 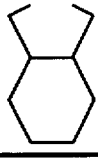 | | 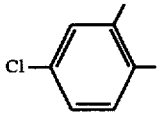 | m.p. 141 C. |

Example VI-I:

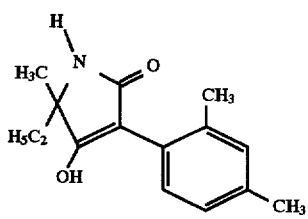

62 g (0.213 mol) of 2-(2,4,6-trimethylphenyl)-N-(1-methoxycarbonyl-2-butyl)-acetamide dissolved in 430 ml of toluene are added dropwise, at reflux temperature, to 12.77 g (0.426 mol) of sodium hydride in 220 ml of absolute toluene, and, once addition is complete, the reaction mixture is boiled at reflux temperature until the starting compound can no longer be detected by thin layer chromatography. Subsequently, ethanol is added dropwise, while cooling with ice, until no further hydrogen is liberated. For the working up, the mixture is concentrated in vacuo, the residue is taken up in absolute ethanol, acidification is carried out at 0° C. to 20° C. using 4N hydrochloric acid, and the precipitate which separates out is filtered off with suction and dried. The crude product which is obtained in this way can be recrystallised from chloroform/n-hexane (1:2).

39.4 g (72 % of theory) of 5-ethyl-5-methyl-3-(2,4,6-trimethylphenyl)-pyrrolidine-2,4-dione are obtained with a melting point of 137°–142° C.

We claim:

1. An N-phenylacetamino nitrile or ester of the formula

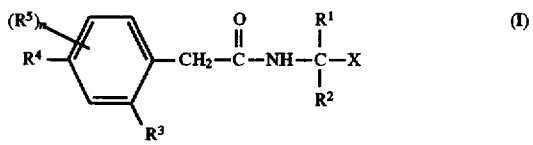

in which

X is CN or —COO—$C_1$-$C_6$-alkyl, $R^1$ and $R^2$, together with the carbon atom to which they are bonded, form an optionally substituted heterocyclyl radical wherein said heterocyclyl radical has 3 to 8 carbon atoms and 1 to 2 heteroatoms selected from the group consisting of oxygen or sulfur and the optional substituents are selected from the group consisting of halogen, straight-chain or branched alkyl having 1 to 6 carbon atoms, straight-chain or branched alkanoyl having 1 to 7 carbon atoms, straight-chain or branched alkanediyl having 3 to 8 carbon atoms, straight-chain or branched dioxyalkylene having 1 to 8 carbon atoms, straight-chain or branched halogenoalkyl having 1 to 6 carbon atoms and 1 to 13 identical or different halogen atoms, straight-chain or branched alkoxy having 1 to 6 carbon atoms, straight-chain or branched alkylthio having 1 to 6 carbon atoms, cycloalkyl having 3 to 8 carbon atoms or aryl having 6 to 10 carbon atoms, $R^3$ represents halogen, alkyl or alkoxy, $R^4$ represents hydrogen, halogen, alkyl, halogenoalkyl or alkoxy, $R^5$ represents halogen, alkyl or alkoxy, and n represents a number 0, 1, 2 or 3.

2. An N-phenylacetamino nitrile or ester according to claim 1,
in which $R^1$ and $R^2$ together with the carbon atom to which they are bonded, represent saturated or unsaturated heterocyclyl having 4 or 5 carbon atoms and 1 to 2 heteroatom heteroatoms selected from the group consisting of O and S and the optional substituents are independently selected from the independently selected from the group consisting of halogen, straight-chain or branched alkyl having 1 to 6 carbon atoms, straight-chain or branched alkanoyl having 1 to 7 carbon atoms, straight-chain or branched alkanediyl having 3 to 8 carbon atoms, straight-chain or branched dioxyalkylene having 1 to 8 carbon atoms, straight-chain or branched halogenoalkyl having 1 to 6 carbon atoms and 1 to 13 identical or different halogen atom, straight-chain or branched alkoxy having 1 to 6 carbon atoms, straight-chain or branched alkylthio having 1 to 6 carbon atoms, cycloalkyl having 3 to 8 carbon atoms and aryl having 6 to 10 carbon atoms, $R^3$ represents fluorine, chlorine, bromine, iodine, straight-chain or branched alkyl having 1 to 8 carbon atoms, or straight-chain branched alkoxy having 1 to 8 carbon atoms, $R^4$ represents hydrogen, fluorine, chlorine, bromine, iodine, straight-chain or branched alkyl having 1 to 8 carbon atoms, straight-chain or branched halogenoalkyl having 1 to 8 carbon atoms and 1 to 17 identical or different halogen atoms, or straight-chain or branched alkoxy having 1 to 8 carbon atoms, $R^5$ represents fluorine, chlorine, bromine, iodine, straight-chain or branched alkyl having 1 to 8 carbon atoms, or straight-chain or branched alkoxy having 1 to 8 carbon atoms, and n represents a number 0, 1, 2 or 3.

3. An N-phenylacetamino nitrile or ester according to claim 1,
in which $R^1$ and $R^2$, together with the carbon atom to which they are bonded, represents saturated or unsaturated heterocyclyl having 4 to 5 carbon atoms and 1 heteroatom selected from the group consisting of O or S and which is optionally substituted once to four times with a substituent independently selected from the group consisting of fluorine, chlorine, bromine, straight-chain or branched alkyl having 1 to 4 carbon atoms, straight-chain or branched alkanoyl having 1 to 5 carbon atoms, straight-chain or branched alkanediyl having 3 to 6 carbon atoms, straight-chain or branched dioxyalkylene having 1 to 6 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched alkylthio having 1 to 4 carbon atoms, cycloalkyl having 3 to 7 carbon atoms, and phenyl, $R^3$ represents fluorine, chlorine, bromine, straight-chain or branched alkyl having 1 to 6 carbon atoms, or straight-chain or branched alkoxy having 1 to 6 carbon atoms, $R^4$ represents hydrogen, fluorine, chlorine, bromine, straight-chain or branched alkyl having 1 to 6 carbon atoms, straight-chain or branched halogenoalkyl having 1 to 6 carbon atoms and 1 to 13 identical or different halogen atoms, or straight-chain or branched alkoxy having 1 to 6 carbon atoms, $R^5$ represents fluorine, chlorine, bromine, straight-chain or branched alkyl having 1 to 6 carbon atoms, or branched alkoxy having 1 to 6 carbon atoms, and n represents a number 0, 1 or 2.

4. An N-phenylacetamino nitrile or ester according to claim 1,
in which

R¹ and R², together with the carbon atom to which they are bonded, represent saturated or unsaturated heterocyclyl having 4 to 5 carbon atoms and 1 heteroatom selected from the group consisting of O or S which is optionally substituted identically or differently once to three times by a substituent independently selected from the group consisting of fluorine, chlorine, bromine, straight-chain or branched alkyl having 1 to 4 carbon atoms, straight-chain or branched alkanoyl, having 1 to 4 carbon atoms, dioxyalkylene having 1 to 3 carbon atoms, halogenoalkyl having 1 to 2 carbon atoms and 1 to 5 identical or different halogen atoms, straight-chain or branched alkoxy having 1 or 2 carbon atoms, straight-chain or branched alkylthio having 1 or 2 carbon atoms, cycloalkyl having 3, 5 or 6 carbon atoms, and phenyl, R³ represents fluorine, chlorine, bromine, straight-chain or branched alkyl having 1 to 4 carbon atoms, or straight-chain or branched alkoxy having 1 to 3 carbon atoms, R⁴ represents hydrogen, fluorine, chlorine, bromine, straight-chain or branched alkyl having 1 to 4 carbon atoms, halogenoalkyl having 1 or 2 carbon atoms and 1 to 5 identical or different halogen atoms, or straight-chain or branched alkoxy having 1 to 3 carbon atoms, R⁵ represents fluorine, chlorine, bromine, straight-chain or branched alkyl having 1 to 4 carbon atoms, or straight-chain or branched alkoxy having 1 to 3 carbon atoms, and n represents a number 0 or 1.

5. An N-phenylacetamino nitrile or ester according to claim 1,
in which
X is CN.

6. An N-phenylacetamino nitrile or ester according to claim 1,
in which
X is —COO—$C_{1-6}$-alkyl.

7. A compound according to claim 1, of the formula

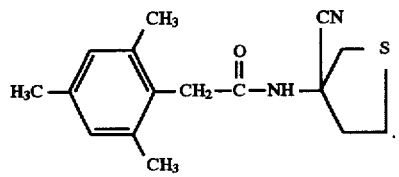

8. A compound according to claim 1, of the formula

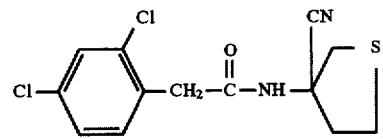

9. A compound according to claim 1, of the formula

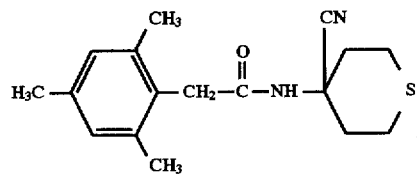

10. A compound according to claim 1, of the formula

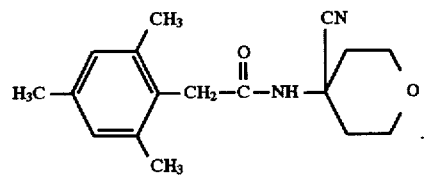

11. A compound according to claim 1, of the formula

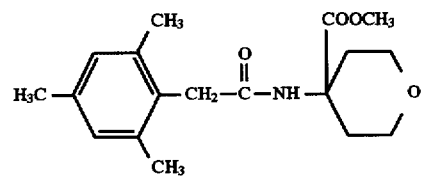

12. A compound according to claim 1, of the formula

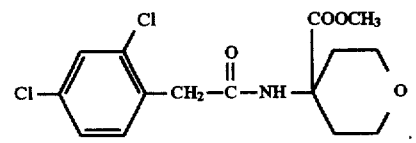

* * * * *